United States Patent

Green et al.

Patent Number: 5,505,363

Date of Patent: Apr. 9, 1996

[54] SURGICAL STAPLES WITH PLATED ANVILS

[75] Inventors: David T. Green, Westport; Henry Bolanos, East Norwalk; Gary S. Kappel, Stamford; Karl H. Ehrenfels, Ridgefield, all of Conn.

[73] Assignee: United States Surgical Corporation, Norwalk, Conn.

[21] Appl. No.: 405,441

[22] Filed: Mar. 15, 1995

Related U.S. Application Data

[63] Continuation of Ser. No. 85,528, Jun. 30, 1993, abandoned, which is a continuation-in-part of Ser. No. 593,654, Oct. 5, 1990, abandoned, which is a continuation-in-part of Ser. No. 358,646, May 26, 1989, Pat. No. 5,040,715.

[51] Int. Cl.⁶ .................................................. A61B 17/068
[52] U.S. Cl. ................................. 227/175.1; 227/19
[58] Field of Search ............................. 227/19, 176, 177, 227/178, 180, 175

[56] References Cited

U.S. PATENT DOCUMENTS 5,160,318  11/1992  Shuler .

OTHER PUBLICATIONS

"Electroless Plating" Publication, *Tool, and Manufacturing Engineers Handbook* (1989).

*Primary Examiner*—Rinaldi I. Rada

[57] ABSTRACT

The present invention relates to anvils for surgical fastener applicators having a fastener forming surface for forming surgical fasteners, an intermediate surface formed of a metallic alloy disposed on at least a portion of the fastener forming surface and a polytetrafluorethylene coating disposed on the intermediate surface. The polytetrafluorethylene coating is provided to reduce the force necessary to form the fasteners.

17 Claims, 9 Drawing Sheets

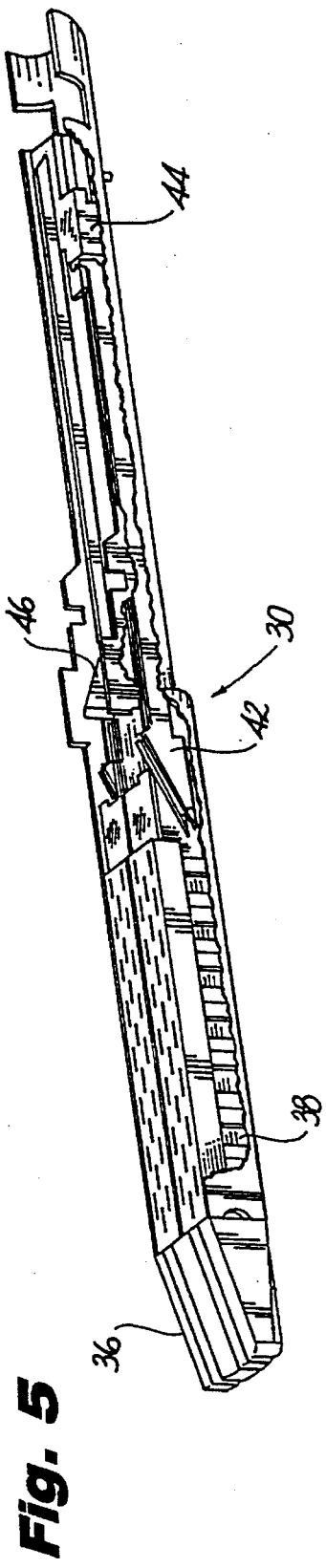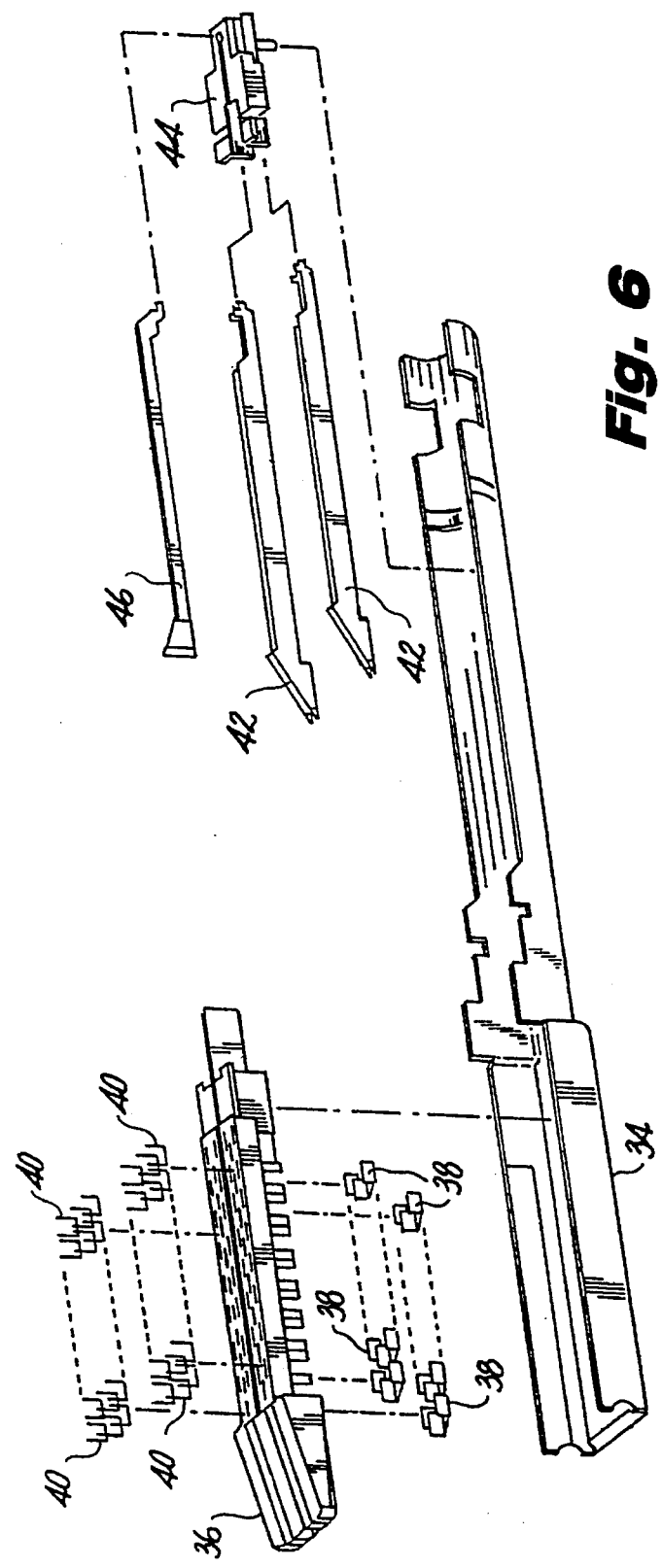

SURGICAL STAPLES WITH PLATED ANVILS

CROSS REFERENCE TO RELATED APPLICATIONS

This is a continuation of application Ser. No. 08/085,528 filed on Jun. 30, 1993, which is a CIP of Ser. No. 07/593,654 filed on Oct. 5, 1990, both abandoned which is a CIP of Ser. No. 07/358,646 filed on May 26, 1989 now U.S. Pat. No. 5,040,715.

BACKGROUND OF THE INVENTION

1. Field of the Invention

This invention relates to plated anvils for surgical fastener applicators, and more particularly to PTFE available under the trademark TEFLON electroless nickel plating of the anvils.

2. Background of the Related Art

Surgical fastener applicators, such as staplers, have been utilized to join body tissue during invasive surgical procedures for some time. For example, in some surgical operations it is necessary to adjoin two hollow body organs alongside each other, generally with their longitudinal axes parallel to each other, and to effect a longitudinal cut through the contacting circumferential walls of the two organs so that the two organs constitute a single hollow chamber along the length of the cut. Correspondingly, the circumferential portions of the two adjoining organs on each lateral side of the cut must be sutured or otherwise attached by at least one line of "stitches" in order to maintain the integrity of the union.

Surgical fastener applicators utilized during the above described procedure provide handle assemblies which allow the surgeon to grasp the instrument in close proximity to the tissue to be adjoined and easily cause actuation of the stapling mechanisms. As a result, the forces required to form the staples have not been a primary design criteria when developing staplers for use in invasive surgical procedures.

On the other hand, endoscopic and laparoscopic procedures have recently advanced to the point where surgeons are performing increasingly complex and innovative surgical procedures using a wide variety of instruments including surgical fastener applicators. For background, in laparoscopic procedures, surgery is performed in the interior of the abdomen through a small incision, whereas in endoscopic procedures, surgery is performed in any hollow viscus of the body, e.g., through narrow endoscopic tubes inserted through small entrance wounds in the skin. Laparoscopic and endoscopic procedures generally require that any instrumentation inserted into the body be sealed, i.e., provisions must be made to ensure that gases do not enter or exit the body through the laparoscopic or endoscopic incision as, for example, in surgical procedures in which the surgical region is insufflated. Moreover, laparoscopic and endoscopic procedures often require the surgeon to act on organs, tissues, and vessels far removed from the incision, thereby requiring that any instruments to be used in such procedures be both long and narrow.

An example of a surgical fastener applicator adapted for such endoscopic and laparoscopic procedures is shown in commonly assigned U.S. Pat. No. 5,040,715 to Green et al. The applicator includes a handle assembly and a tubular portion having a jaw assembly positioned at its distal end. In one embodiment, the jaw assembly includes an anvil portion as one jaw and a fastener cartridge assembly as the other jaw. Generally, the fastener cartridge assembly has two, triple staggered rows of fasteners, such as staples, and a pusher bar/knife assembly between the two triple staggered rows. Since the general construction of the above described endoscopic applicator results in jaw assemblies which are removed from the handle assembly by a significant distance, the force required to form the staples has become a factor to be considered when designing these instruments.

As will be discussed in further detail below, copending Application Ser. No. 07/593,654, filed Oct. 5, 1990, discloses anvils plated with a metallic alloy which moderately reduced the force required to form the staples. However, further reduction of the requisite force necessary to form the staples is desirable.

SUMMARY OF THE INVENTION

The present invention provides an anvil for surgical fastener applicators, which comprises a fastener forming support member having at least a portion thereof configured and dimensioned to form at least one surgical fastener. The fastener forming support member includes at least one fastener forming depression corresponding to each surgical fastener so as to facilitate formation of the surgical fasteners. Preferably, the surgical fastener forming portion has a layer of a hardened material formed thereon and a layer of a friction reducing material disposed on the layer of hardened material. The layer of hardened material is formed from a metallic alloy or from ceramic, while the friction reducing layer is preferably formed of PTFE.

In an alternative embodiment, the anvil of the present invention comprises an anvil plate of monolithic construction having a staple forming surface defined thereby and a plurality of staple forming depressions formed on the staple forming surface for forming a plurality of surgical staples. An intermediate surface portion formed of a metallic alloy disposed on at least a portion of the staple forming depressions, and an outer surface portion formed of PTFE disposed on the intermediate surface portion are also provided.

The present invention also provides a surgical apparatus for driving surgical fasteners into body tissue. The apparatus comprises a frame and an endoscopic portion defining a longitudinal axis and extending distally from the frame. Preferably, the endoscopic portion includes an elongated support having a distal member for receiving a cartridge assembly having a tissue engaging surface, an anvil member having a fastener forming surface and a proximal end thereof retained in the elongated support and relatively movable between an open position and a closed position wherein the fastener forming surface is in close cooperative alignment with the tissue engaging surface of the cartridge assembly. The apparatus also includes means for effecting relative movement of the anvil member between the open position and closed position, and means for ejecting the surgical fasteners from the cartridge assembly, so that the surgical fasteners engage the fastener forming surface.

Additionally, the present invention relates to a method for forming surgical stapler anvils which reduce the force required to form surgical staples. The method includes the following steps, providing anvil means having a staple forming surface for forming at least one surgical staple, applying a layer of a hardened material to the staple forming surface and applying a PTFE coating to the layer of hardened material.

A method for reducing friction between camming surfaces of surgical instruments is also provided, which comprises applying a layer of a hardened material to at least one camming surface of the surgical instrument and applying a PTFE coating to the layer of hardened material.

BRIEF DESCRIPTION OF THE DRAWINGS

Preferred embodiments of the invention are described hereinbelow with reference to the drawings wherein:

FIG. 5 is a perspective view of an assembled cartridge assembly;

FIG. 6 is a perspective view with parts separated of the cartridge assembly of FIG. 5;

DETAILED DESCRIPTION OF THE PREFERRED EMBODIMENTS

Generally, a wide variety of surgical fasteners are contemplated for use with anvils configured in accordance with the present invention. Additionally, the plated anvils to be discussed below are adaptable for use with numerous types of surgical staplers or other types of instruments which apply fasteners to body tissue, i.e., staplers utilized for endoscopic, laparoscopic and/or conventional invasive surgical procedures. For the purposes of this detailed description, the surgical fastener applicator, the anvil and the staple cartridge which will be discussed and shown in the Figs. are described in commonly assigned U.S. patent application Ser. No. 07/593,654 to Green et al. filed Oct. 5, 1990 which is incorporated herein by reference. However, it should be noted that the PTFE coating of anvils according to the present invention is not limited to the surgical stapler anvil described in the above mentioned patent application, i.e., the coating of other types of anvils is contemplated.

Figure 1:
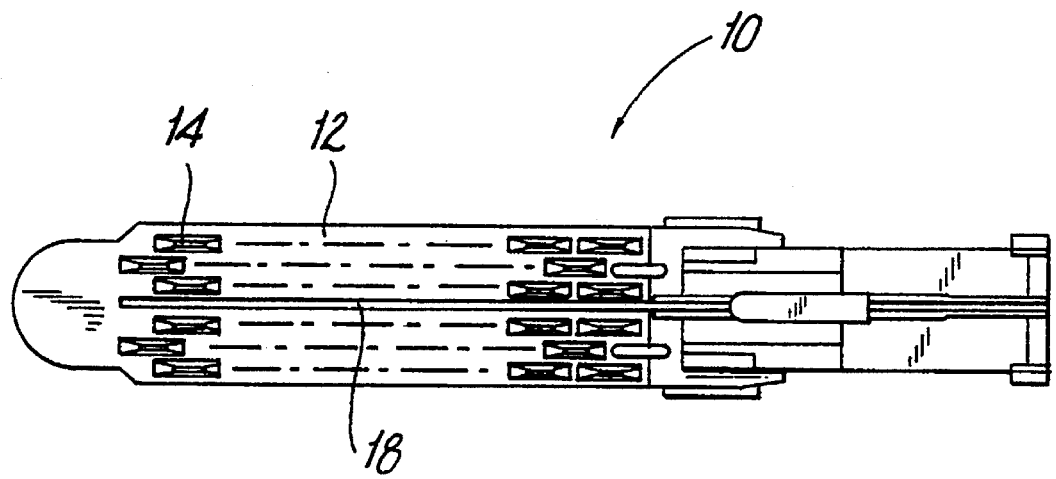
FIG. 1 is a top plan view of an exemplary surgical stapler anvil, illustrating the tissue contacting surface and the fastener forming depressions.
Figure 2:
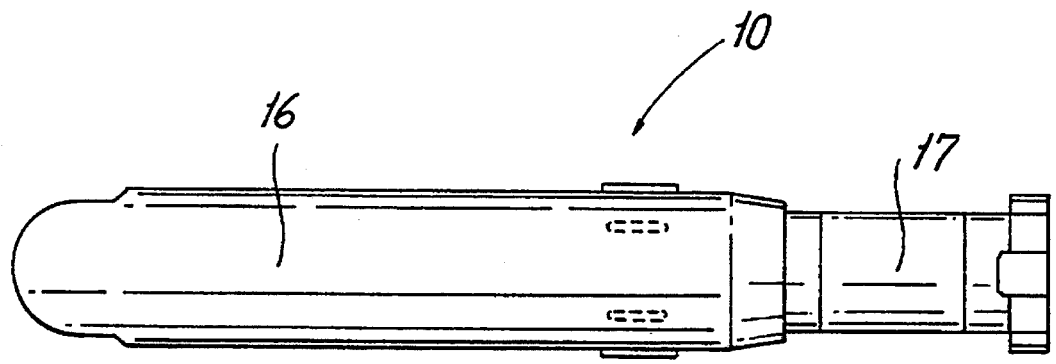
FIG. 2 is a bottom plan view of the anvil of FIG. 1, illustrating the anvil plate.
Figure 3:
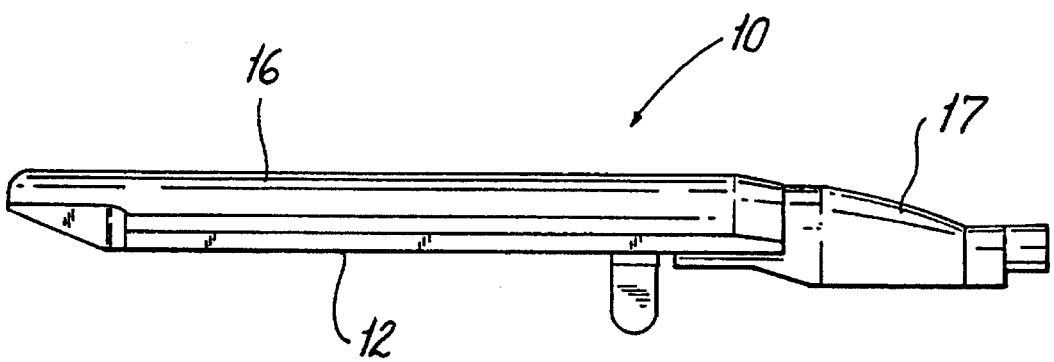
FIG. 3 is a side view of the anvil of FIG. 1.

Referring to FIGS. 1–3, an exemplary anvil assembly is shown. The anvil assembly 10 includes tissue contacting surface 12, fastener forming depressions 14 and anvil plate 16. Anvil assembly 10 may be of monolithic construction where tissue contacting surface 12 is formed into anvil plate 16, or anvil assembly 10 may be fabricated by joining or securing the tissue contacting surface to the anvil plate. As shown, fastener forming depressions 14 in tissue contacting surface 12 are spatially arranged in three rows on each side of center channel 18 and are provided to facilitate formation of the fasteners.

The proximal end of anvil plate 16 includes camming surface 17 which pivots anvil assembly 10 between open and closed positions, as will be described in more detail below.

Figure 4:
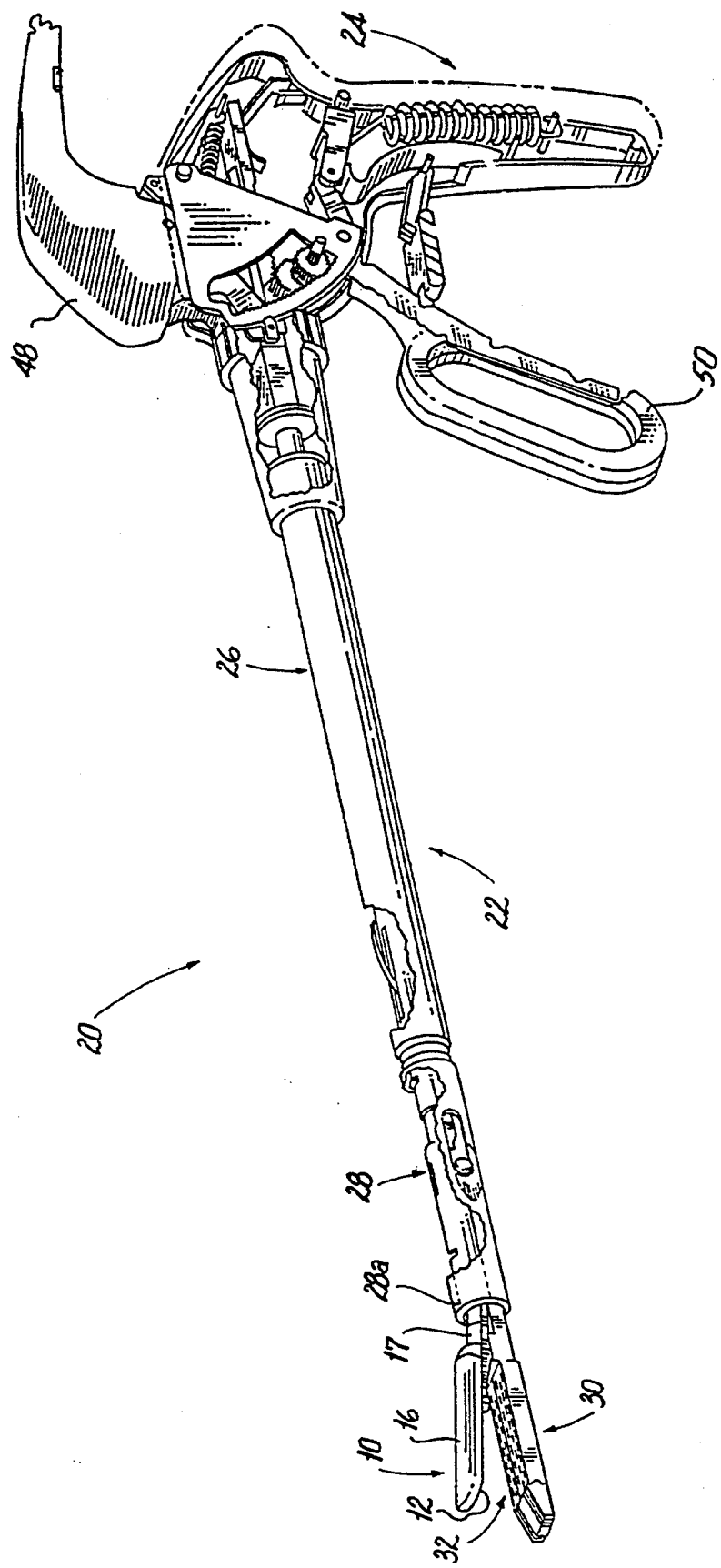
FIG. 4 is a perspective cutaway view of an exemplary, assembled stapler apparatus utilizing the anvil of the present invention.

Referring to FIG. 4, the exemplary surgical fastener apparatus 20 described in U.S. Pat. No. 5,040,715 to Green et al. includes endoscopic section 22 and frame 24. Generally, endoscopic section 22 includes cover tube portion 26 located at the proximal end thereof and collar tube portion 28 located adjacent the distal end thereof.

Cover tube portion 26 and collar tube portion 28 are provided to house the internal mechanisms which place and form the fasteners. In addition, collar tube 28 is configured to move distally and cam against anvil plate 16 in response to pivotal movement of clamp handle 48. Anvil assembly 10 is mounted for pivotal movement and is at least partially surrounded by collar tube 28. Fastener cartridge assembly 30 is removably secured to cover tube portion 26 and is at least partially surrounded by collar tube 28. As such, cartridge assembly 30 and anvil assembly 10 are adapted to be arranged in a substantially parallel orientation (subject to a preferred precamber which is imparted to the anvil assembly) so that tissue contacting surface 12 of anvil assembly 10 is in substantial cooperative alignment with tissue engaging surface 32 of cartridge assembly 30.

To reduce the wear between camming surface 17 and collar tube 28 and to reduce the force required to cause the pivotal movement of anvil plate 16, camming surface 17 and interior surface 28a of collar tube 28 are initially coated with a metallic alloy by an electroless plating process, with ceramic by spray deposition or with an equivalent type of material having a similar hardness value. Examples of suitable metallic alloys include nickel, gold, silver, titanium nitride and chromium.

The thickness of the initial coating is dependent on the composition and inherent characteristics of the coating material. For example, where nickel is used, the applied surface is preferably in the range of between about 0.0003 and about 0.0004 inches in thickness. Where ceramic is used, the applied surface is also preferably in the range of between about 0.0003 and about 0.0004 inches in thickness.

Electroless plating, also known as autocatalytic deposition, deposits a substantially uniform coating onto catalytic surfaces, regardless of the shape of the part. After a primary layer of metal or alloy has been formed onto the catalytic surface, that primary layer becomes a catalyst which continues the reaction. Similarly, after each subsequent layer has formed, that subsequent layer becomes a catalyst which continues the reaction. Deposition of the metal or alloy onto the surface occurs in an aqueous solution containing metal ions, a reducing agent and a catalyst. Chemical reactions caused by the reducing agent and catalyst within the aqueous solution cause deposition of the metal or alloy onto the surface. As noted, the coating on the surfaces within the aqueous solution is substantially uniform and the thickness of the coating is determined by the length of time the surface or surfaces are immersed within the solution.

To further reduce the wear between camming surfaces and/or the force required to form the staples, a PTFE coating, otherwise known as PTFE available under the trademark TEFLON which is manufactured by DuPont, is applied to the initial metallic alloy or ceramic coating. However, other known friction reducing materials are also contemplated. Preferably, the thickness of the PTFE coating on camming surface 17 and interior surface 28a of collar tube 28 is in the range between about 0.0001 and about 0.0003 inches. In addition to reducing the force required to form the staples, the PTFE coated anvil assemblies also provide consistent firing forces of the instrument, thus minimizing misfirings of the staples during continuous use of the anvil assembly.

Referring now to FIGS. 5 and 6, cartridge assembly 30 includes cartridge housing 34, cartridge 36 having a plurality of pushers 38 and fasteners 40 disposed in longitudinal arrangement therein, a plurality of cam bars 42 removably disposed in cam bar adapter 44 and knife 46 mounted in the cam bar adapter 44. Cam bar adapter 44 is operatively connected to firing handle 50 such that pivotal movement of firing handle 50 causes placement and formation of fasteners 40. Commonly assigned U.S. Pat. No. 4,978,049 to Green describes in greater detail a preferred cartridge assembly of the invention, and is incorporated herein by reference.

In operation, the surgical fastener apparatus is inserted into the patient, preferably through an endoscopic tube which is adapted to effectively maintain a sealed relationship with the endoscopic portion of the instrument. The jaws of the instrument are closed for insertion into the endoscopic tube, either by pinching anvil assembly 10 and cartridge assembly 30 together prior to insertion or by closing the clamping mechanism prior to insertion.

Once inserted into the body cavity, anvil assembly 10 and cartridge assembly 30 are returned to the open position. The jaws are then oriented to capture the object tissue. Once the tissue is properly placed within the jaws, i.e., between anvil assembly 10 and cartridge assembly 30, clamp handle 48 of frame 24 is pivoted downward until it locks in place within the frame. This pivotal motion of clamp handle 48 causes collar tube 28 to move distally relative to frame 22. As a result, anvil assembly 10 is pivoted toward cartridge assembly 30 so that the tissue is firmly maintained between the jaws.

To place the staples and cut the tissue, firing handle 50 is pivoted proximally toward frame 24. This pivotal motion causes cam bar adapter 44, cam bars 42 and knife 46 to move distally so that cam bars 42 engage pushers 38 and sequentially drive and form fasteners 40 and so that knife 46 advances distally and cuts the tissue.

Generally, the anvil assemblies of the present invention are also initially coated with a hardened material having a hardness value which is similar to those described above. In one embodiment, the anvil assembly is initially coated with a metallic alloy by an electroless plating process as described above. However, other known plating and/or coating techniques may be utilized to cause deposition of metals or alloys onto a surface. In one embodiment particularly useful with titanium fasteners, it has been found that forming of the fasteners against and within the fastener forming depressions of the anvil is facilitated by applying a hard, relatively smooth surface on the fastener forming portion of the anvil. The preferred method of application of this surface is by electroless plating, with the surface being formed of a metallic alloy such as, for example, nickel, gold, silver, titanium nitride or chromium. Where nickel is used, the applied surface is preferably in the range of 100µ–2000µ in thickness with an optimum thickness of between 200µ–500µ. As noted above, ranges for other alloys may vary depending upon their inherent characteristics.

Where nickel is to be applied to the staple forming portion of the anvil, the preferred method is an electroless plating method including the steps of: electrocleaning the anvil in a cyanide-containing cleaner, reversing polarity at predetermined intervals, preferably about every 10–15 seconds, at a current of about 50 amps/ft$^2$; rinsing thoroughly; rinsing in a solution containing a strong acid, preferably 20% HCl, dipping several times; immersing anvil in a NiCl strike tank for plating, preferably for two to four minutes at a current of about 50 amps/ft$^2$; rinsing; and immersing the anvil in an electroless Ni bath, preferably Enthone 418 or 431, for a time sufficient to achieve the desired plating thickness. For example, at a deposition rate of 0.0005 in/hr, a time of between 30 to 40 minutes would be required to achieve a thickness of about 300µ±50µ. Other coating procedures are also contemplated including vapor deposition, etc., and are encompassed by the present invention.

In an alternative embodiment, the anvil assemblies of the present invention are initially coated with ceramic which also reduces the force required to form the staples as well as reduces the wear on the staple forming surface. Preferably, the ceramic coating is formed on the anvil by spray deposition. Preferably, the thickness of the ceramic coating is in the range of between about 0.0003 and about 0.0004 inches.

To further reduce the force required to form the staples, a PTFE coating is applied to the initial metallic alloy or ceramic coating. Preferably, the thickness of the PTFE coating is in the range between about 0.0001 and about 0.0003 inches. As noted above, in addition to reducing the force required to form the staples, the PTFE coated anvil assemblies also provide consistent firing forces of the instrument, thus minimizing misfirings of the staples during continuous use of the anvil assembly.

EXAMPLES

I. Parameters

Figure 7:
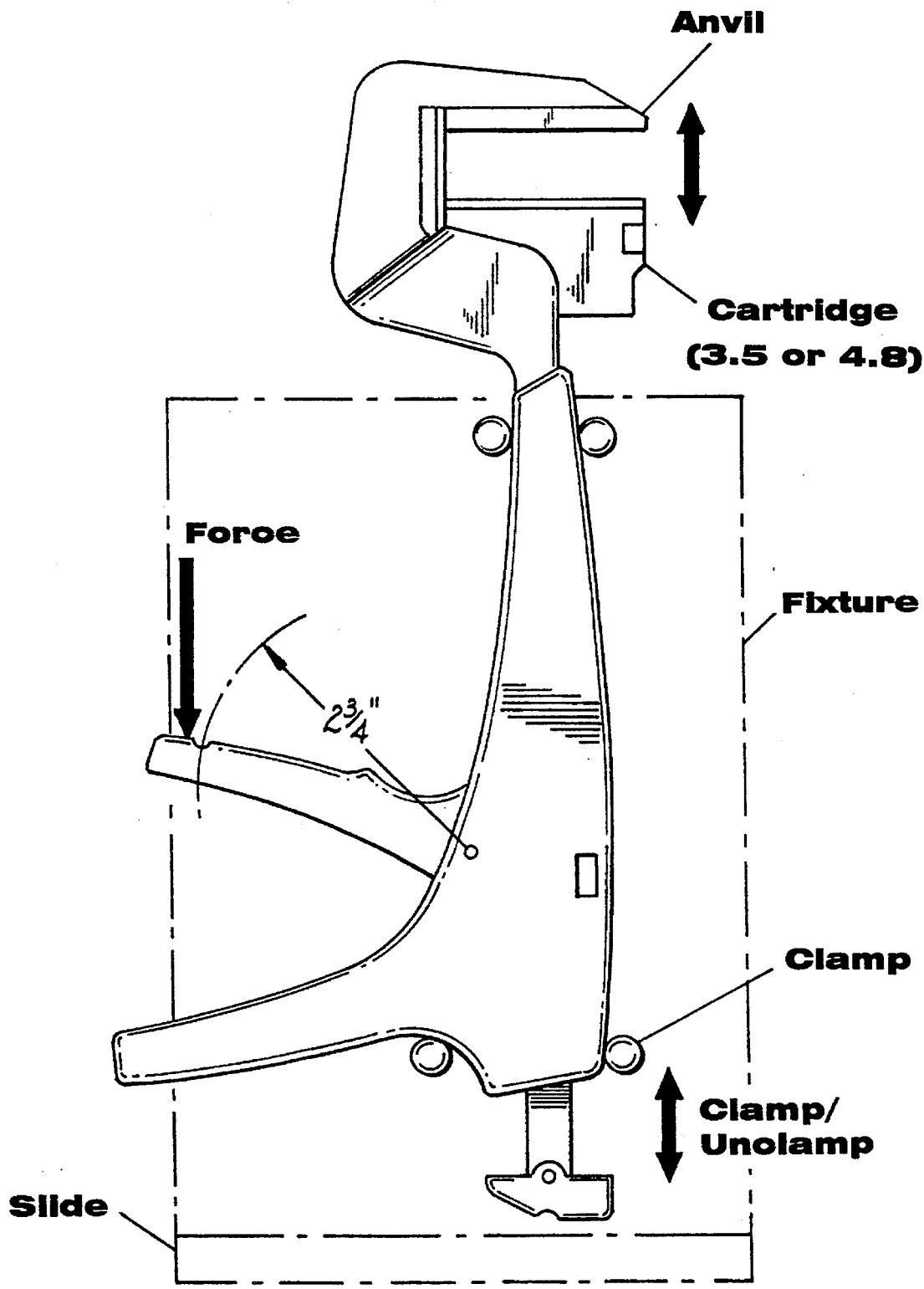
FIG. 7 is a side view of the test instrument and test fixture utilized in the examples.

A surgical stapling instrument was fixtured in an Automated Materials Testing System, manufactured by Instron Corporation, as shown in FIG. 7, for a force to form staples test on electroless nickel plated and PTFE electroless nickel plated anvil assemblies. Tests were conducted with 4.8 mm titanium staples and 3.5 mm titanium staples. The staple size designation refers to the height of the staple leg before formation. In the case of the 3.5 mm staples, the backspan was 3 mm and the wire was 0.21 mm in diameter. In the case of the 4.8 mm staples, the backspan was 3 mm and the wire was 0.24 mm in diameter.

II. Results

A. Tests using 4.8 mm staples

Figure 8:
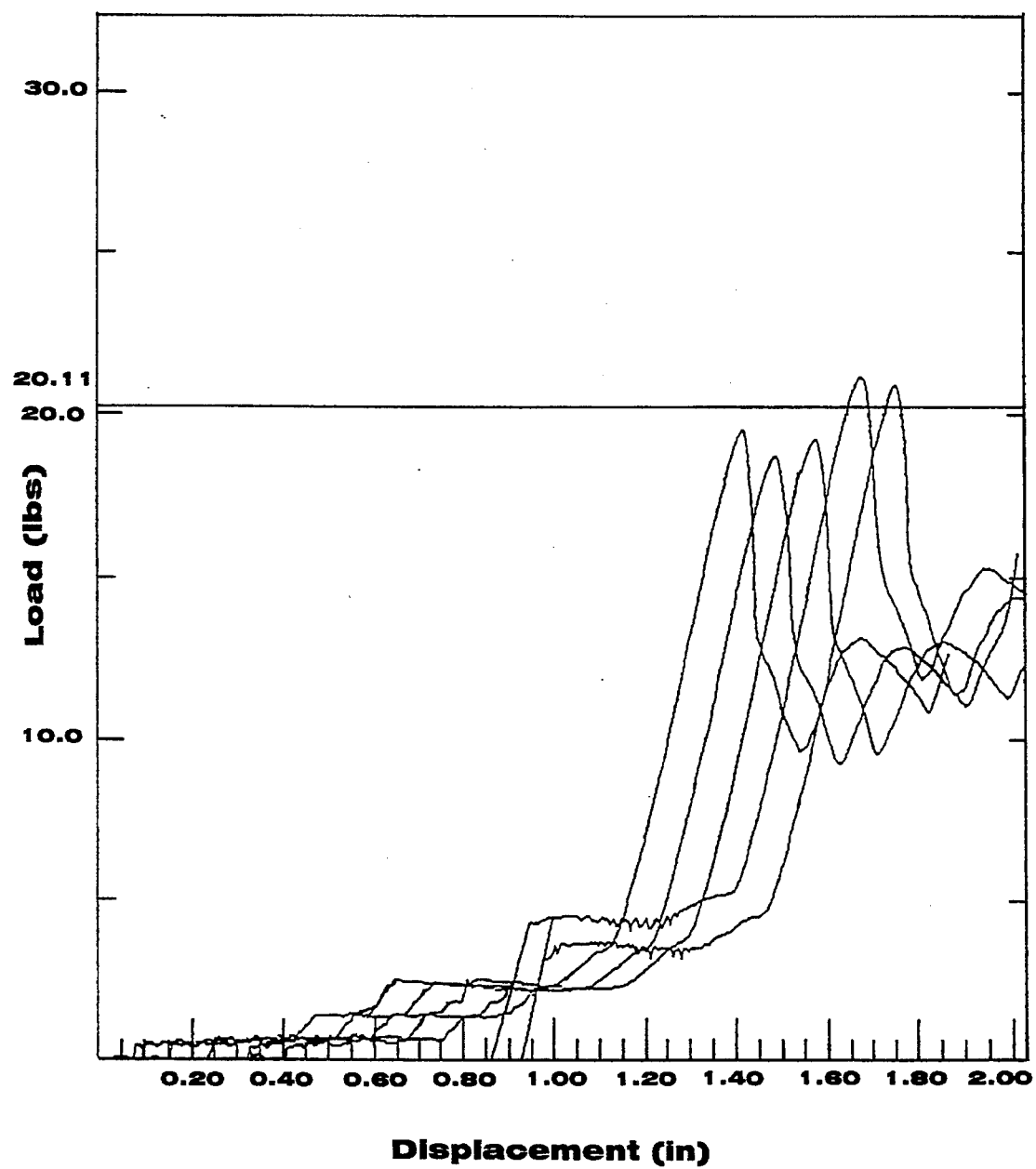
FIG. 8 is a graph, illustrating the load required to form a first group of 4.8 mm staples against a PTFE electroless nickel plated anvil.

A first group of five staple cartridges were fired using the PTFE electroless nickel plated anvil assembly. As shown by the load/displacement graph in FIG. 8, the average load required to form the staples was 20.11 lbs.

Figure 9:
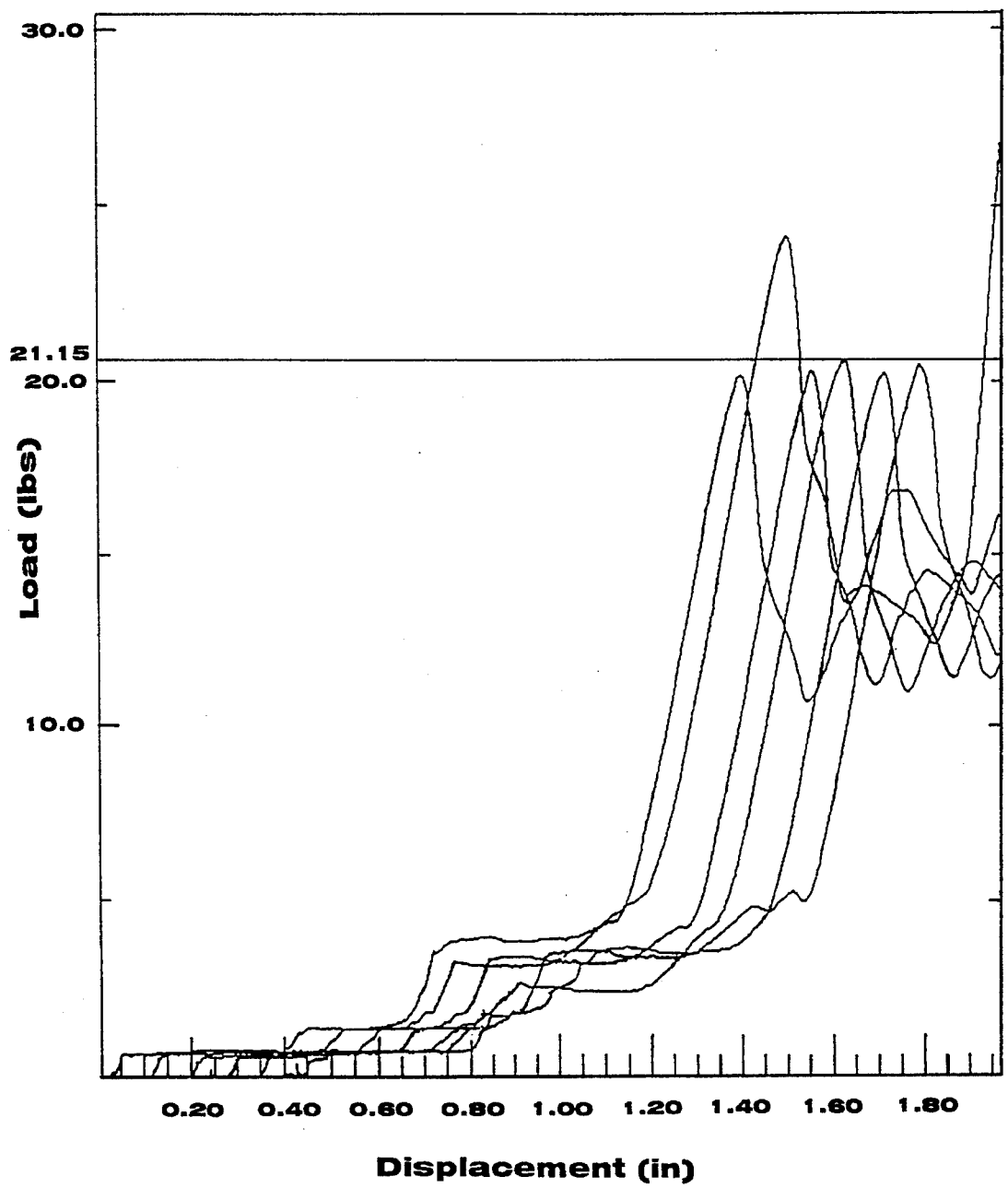
FIG. 9 is a graph, illustrating the load required to form a second group of 4.8 mm staples against a PTFE electroless nickel plated anvil.

A second group of five staple cartridges were fired using the same PTFE electroless nickel plated anvil. As shown by the load/displacement graph in FIG. 9, the average load required to form the staples was 21.15 lbs.

It should be noted that the first group of firings correspond to the first five firings of staple cartridges against the PTFE electroless nickel plated anvil assembly. The second group of firings correspond to the eleventh through the fifteenth firings of staple cartridges against the PTFE electroless nickel plated anvil assembly. The sixth through the tenth firings of staple cartridges against the same PTFE, electroless nickel plated anvil assembly were not recorded.

Figure 10:
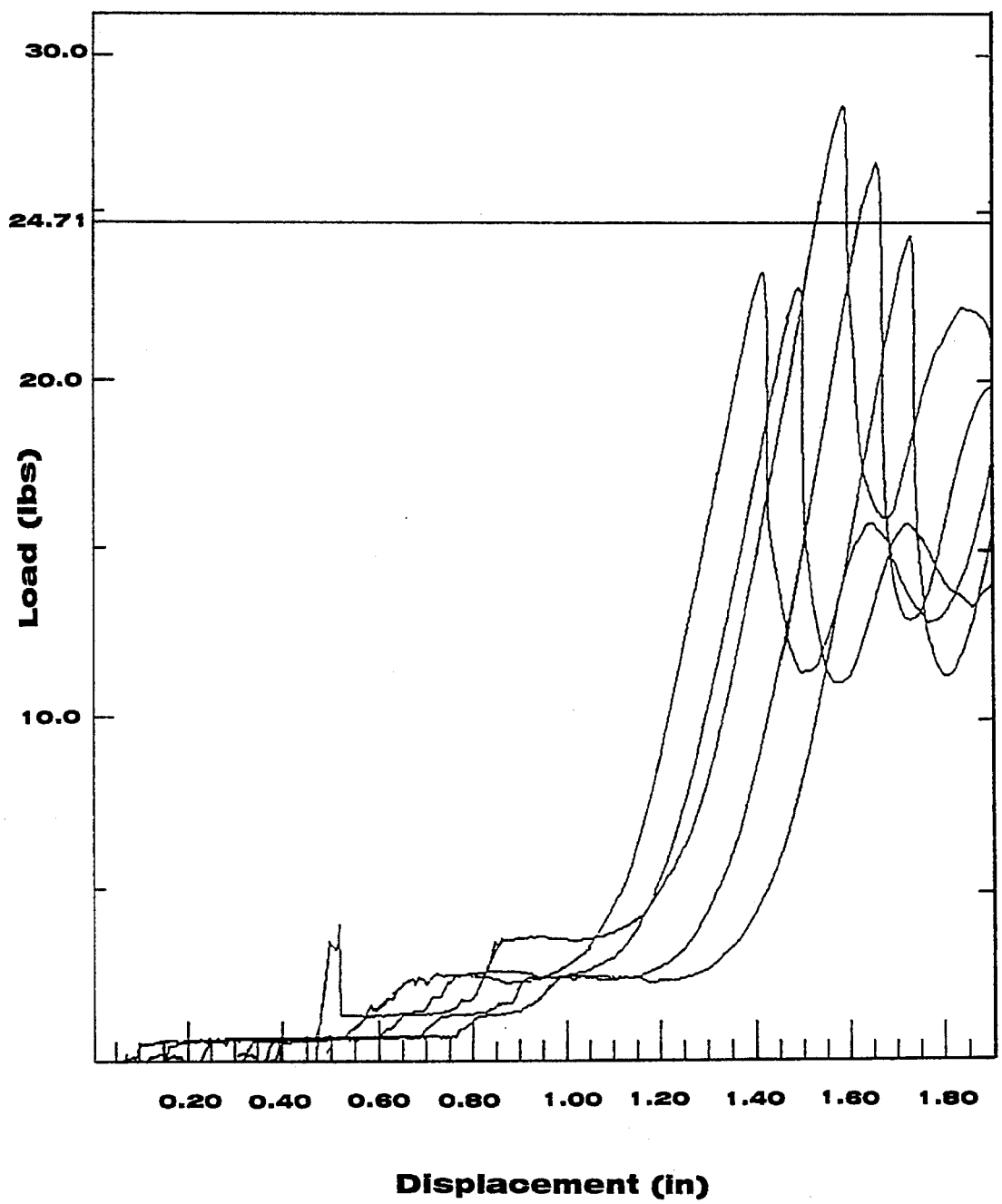
FIG. 10 is a graph, illustrating the load required to form 4.8 mm staples against an electroless nickel plated anvil.

A third group of five staple cartridges were fired using the electroless nickel plated anvil, i.e., without the PTFE surface coating. As shown by the load/displacement graph in FIG. 10, the average lead required to form the staples was 24.71 lbs.

The results of these tests are presented in Table I which shows the maximum lead in pounds applied to each staple cartridge for each group of tests. The average force required to form Group 1 staples was 23% lower than the average force required to form Group 3 staples. Further, the continued use of the same anvil assembly in Group 2 still resulted in a significant reduction of the force required to form the staples. The average force required to form Group 2 staples was 17% lower than the force required to form the staples in Group 3.

TABLE I

| Group 1 | | Group 2 | | Group 3 | |
| --- | --- | --- | --- | --- | --- |
| Staple Cartridge Number | Maximum Load (lbs.) | Staple Cartridge Number | Maximum Load (lbs.) | Staple Cartridge Number | Maximum Load (lbs.) |
| 1 | 19.51 | 1 | 24.18 | 1 | 22.93 |
| 2 | 18.75 | 2 | 20.29 | 2 | 22.53 |
| 3 | 21.21 | 3 | 20.58 | 3 | 27.86 |
| 4 | 20.97 | 4 | 20.33 | 4 | 26.19 |
| 5 | 19.30 | 5 | 20.46 | 5 | 24.04 |
| average force = 19.94 lbs. | | average force = 21.15 lbs. | | average force = 24.71 lbs. | |

B. Tests using 3.5 mm staples

Figure 11:
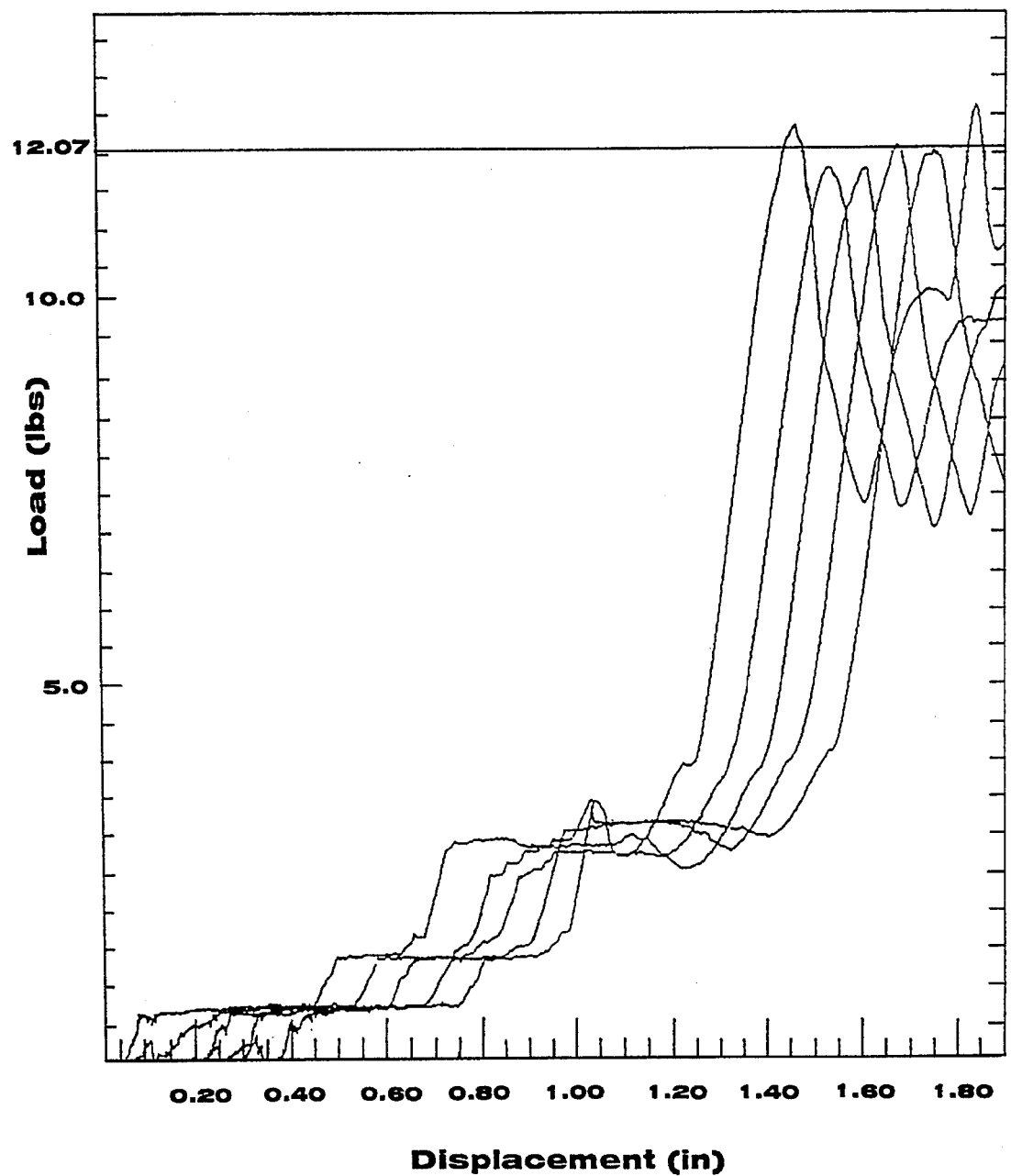
FIG. 11 is a graph, illustrating the load required to form 3.5 mm staples against a PTFE electroless nickel plated anvil.

A first group of five staple cartridges were fired using the PTFE electroless nickel plated anvil assembly. As shown by the load/displacement graph in FIG. 11, the average load required to form the staples was 12.07 lbs.

Figure 12:
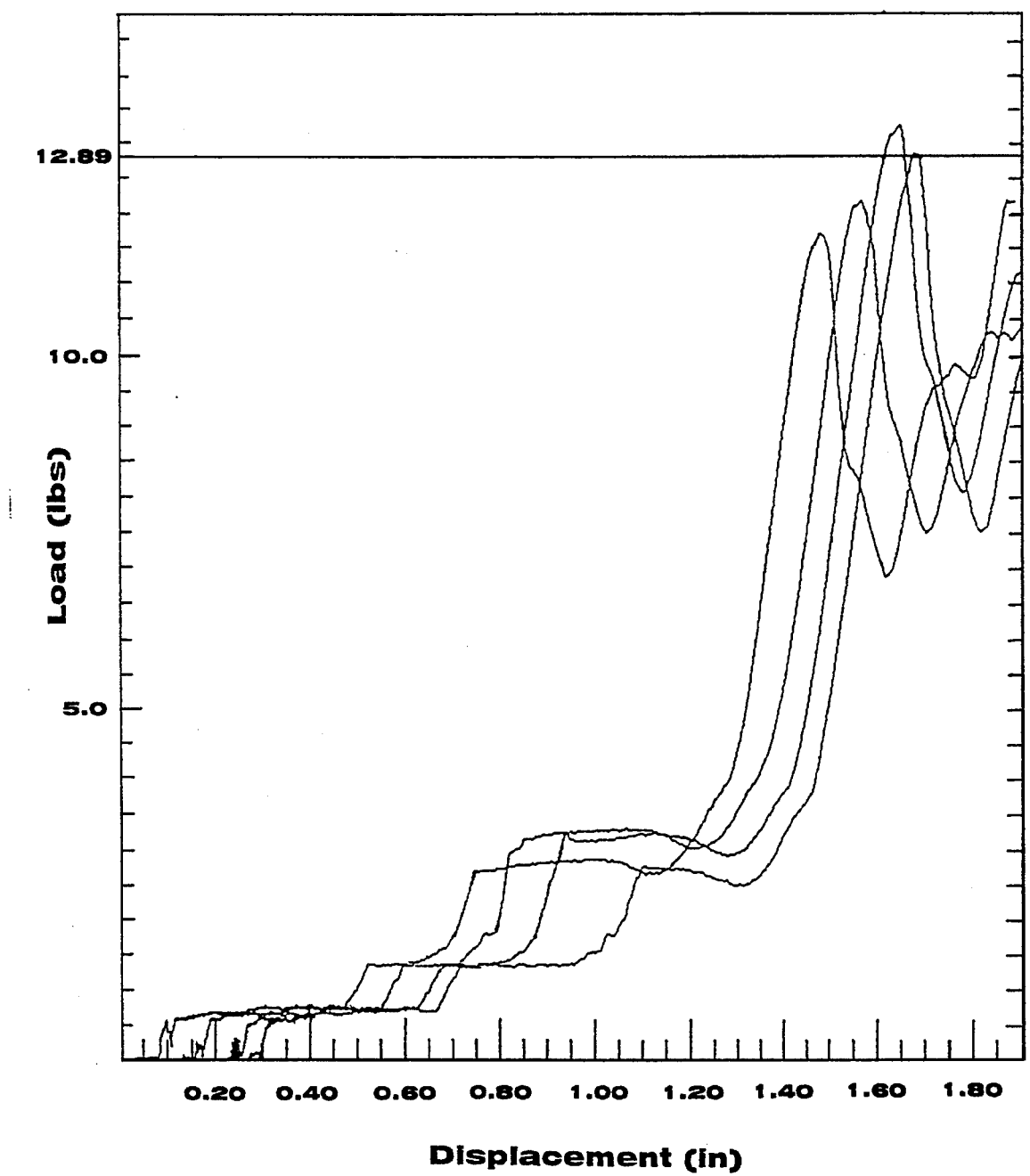
FIG. 12 is a graph illustrating the load required to form 3.5 mm staples against an electroless nickel plated anvil.

A second group of four staple cartridges were fired using the electroless nickel plated anvil assembly. As shown by the load/displacement graph in FIG. 12, the average load required to form the staples was 12.89 lbs.

The results of these tests are presented in Table II which shows the maximum load in pounds applied to each staple cartridge for each group of tests. The force required to form Group 1 staples was 7% lower than the force required to form Group 2 staples.

TABLE II

| Group 1 | | Group 2 | |
| --- | --- | --- | --- |
| Staple Cartridge Number | Maximum Load (lbs.) | Staple Cartridge Number | Maximum Load (lbs.) |
| 1 | 12.65 | 1 | 12.22 |
| 2 | 11.81 | 2 | 12.59 |
| 3 | 11.80 | 3 | 13.24 |
| 4 | 12.08 | 4 | 13.50 |
| 5 | 12.01 | | |
| average force = 12.07 lbs. | | average force = 12.89 lbs. | |

It will be understood that various modifications can be made to the embodiments of the present invention herein disclosed without departing from the spirit and scope thereof. For example, various sizes and types of anvils are contemplated, as well as various types of metallic alloys. Therefore, the above description should not be construed as limiting the invention but merely as exemplifications of preferred embodiments thereof. Those skilled in the art will envision other modifications within the scope and spirit of the present invention as defined by the claims appended hereto.

What is claimed is:

1. An anvil for surgical fastener applicators, said anvil comprising a fastener forming support member at least a portion thereof including a surgical fastener forming surface having fastener forming depressions to form at least one surgical fastener driven thereagainst, said surgical fastener forming surface having an intermediate surface portion formed of a hardened material disposed on at least a portion of said fastener forming depressions and an outer surface portion formed of a friction reducing material disposed on said intermediate surface portion of hardened material.

2. The anvil according to claim 1, wherein said layer of hardened material is formed from a metallic alloy.

3. The anvil according to claim 2, wherein said metallic alloy is selected from the group consisting of nickel, gold, silver, titanium nitride and chromium.

4. The anvil according to claim 2, wherein said layer of metallic alloy is in the range of between about 100μ and about 2000μ in thickness.

5. The anvil according to claim 2, wherein said metallic alloy is applied by electroless plating.

6. The anvil according to claim 2, wherein said metallic alloy is applied by vapor deposition.

7. The anvil according to claim 1, wherein said layer of hardened material is formed from ceramic.

8. The anvil according to claim 7, wherein said layer of ceramic is in the range of between about 0.0003 and about 0.0004 inches in thickness.

9. The anvil according to claim 7, wherein said layer of ceramic is applied by spray deposition.

10. The anvil according to claim 1, wherein said layer of friction reducing material comprises PTFE.

11. The anvil according to claim 1, wherein said layer of PTFE is in the range of between about 0.0001 and about 0.0003 inches in thickness.

12. An anvil for a surgical stapler which comprises:
   an anvil plate of monolithic construction having a staple forming surface defined thereby;
   a plurality of staple forming depressions formed on said staple forming surface for forming a plurality of surgical staples;
   an intermediate surface portion formed of a metallic alloy disposed on at least a portion of said staple forming depressions; and
   an outer surface portion formed of PTFE disposed at least on said intermediate surface portion.

13. The anvil according to claim 12, wherein said intermediate surface portion is formed from a material selected from the group consisting of nickel, gold, silver, titanium nitride and chromium.

14. The anvil according to claim 13, wherein said intermediate surface portion is in the range of between about 100μ and about 2000μ in thickness.

15. The anvil according to claim 12, wherein said metallic alloy is applied by electroless plating.

16. The anvil according to claim 12, wherein said metallic alloy is applied by vapor deposition.

17. The anvil according to claim 12, wherein said outer surface is in the range of between about 0.0001 and about 0.0003 in thickness.

* * * * *